United States Patent [19]

Barth et al.

[11] Patent Number: 4,980,351

[45] Date of Patent: Dec. 25, 1990

[54] 3-AMINOPROPOXYARYL DERIVATIVES HAVING CARDIOTONIC AND ANTIHYPERTENSIVE USE AND COMPOSITIONS THEREOF

[75] Inventors: Hubert G. K. Barth, Emmendingen, Fed. Rep. of Germany; Ila Sircar, Ann Arbor, Mich.

[73] Assignee: Warner-Lambert Company, Morris Plains, N.J.

[21] Appl. No.: 117,252

[22] Filed: Nov. 4, 1987

[51] Int. Cl.$^5$ ............... A61K 31/47; C07D 401/12; C07D 403/12
[52] U.S. Cl. ............... 514/253; 514/218; 514/311; 514/312; 514/314; 590/575; 544/363; 546/156; 546/153; 546/169; 546/170; 546/177
[58] Field of Search ............ 544/363; 540/575; 546/153, 156, 169, 170, 177; 514/253, 218, 311, 312, 314

[56] References Cited

FOREIGN PATENT DOCUMENTS

| 0025111 | 3/1981 | European Pat. Off. . |
| 2139107 | 2/1973 | Fed. Rep. of Germany . |
| 2091262 | 7/1982 | United Kingdom . |
| 2163150 | 2/1986 | United Kingdom . |

OTHER PUBLICATIONS

Bennur, et al., "Chemical Abstracts," vol. 84, 1976, col. 84:17268a.

Agarwal, et al., "Chemical Abstracts," vol. 98, 1983, Col. 98:53648x.

Mehrotra, et al., "Chemical Abstracts" vol. 98, , Col. 98:143248w.

*Primary Examiner*—Richard L. Raymond
*Assistant Examiner*—James H. Turnipseed
*Attorney, Agent, or Firm*—Joan Thierstein

[57] ABSTRACT

The present invention are novel 3-aminopropoxyaryl derivatives, compositions and methods of use thereof for treating congestive heart failure, coronary heart disease, or myocardial ischemia.

6 Claims, No Drawings

3-AMINOPROPOXYARYL DERIVATIVES HAVING CARDIOTONIC AND ANTIHYPERTENSIVE USE AND COMPOSITIONS THEREOF

BACKGROUND OF THE INVENTION

Substituted-2(1H-quinolinones having cardiotonic, antihypertensive, and antithrombotic utility are described in U.S. Ser. No. 846,410, filed Mar. 31, 1986, now pending. Also known are 3-aminopropoxyaryl derivatives having a heterocyclic ring system which are indicated for use as cardiotonic, antiarrhythmic, $\alpha$- and $\beta$-adrenoceptor blocking, and calcium antagonistic agents in Sandoz, Ltd., British application No. 2163150 which cites European patent Specification No. 25111 and British patent Specification No. 2,091,262. Various heterocyclic ring systems are substituents known in agents for treating circulatory conditions, for example, such substituents are known on an adenosine substrate having coronary and circulatory activity from a disclosure in Merck's German application No. 2,139,107. However, the disclosures teach compounds understood by an ordinarily skilled artisan to have different mechanisms of action and thus, there are no disclosures which in any way teach or make obvious the novel compounds of the present invention.

SUMMARY OF THE INVENTION

The present invention is a compound of formula (I)

$$Ar-OCH_2CH(OH)-CH_2NR_1R_2 \quad I$$

wherein $R_1$ and $R_2$ are independently
(i) lower alkyl, aralkyl, cycloalkyl;
(ii) taken together may form a 5-, 6-, or 7-membered ring optionally substituted by lower alkyl, aralkyl, hydroxy, mercapto, aryl, monoloweralkylamino or diloweralkylamino, for example, of the formula (II)

wherein $R_3$ and $R_4$ are independently hydrogen, lower alkyl, aralkyl, cycloalkyl and wherein $R_5$ and Q are independently hydrogen, lower alkyl or together form an additional bond; (iii) then together may form wherein m is 1 or 2 and $R_6$ is (a) lower alkyl substituted by one or two aryl groups, or (b) aryl optionally substituted by lower alkyl, halogen, trifluoromethyl, lower alkoxy; and (c)

$$\overset{O}{\underset{\|}{C}}R_7$$

wherein
$R_7$ is lower alkyl, lower alkoxy, or monoloweralkylamino, or diloweralkylamino; and wherein Ar is of the formula wherein X, Y, and Z are independently hydrogen, lower alkyl, halogen, trifluoromethyl, $$\overset{O}{\underset{\|}{C}}OR_8$$

wherein $R_8$ is lower alkyl, $$\overset{O}{\underset{\|}{C}}NH_2,$$

or cyano and pharmaceutically acceptable salts thereof

The preferred compounds of the present invention are of formula I wherein $NR_1R_2$ is and although the position at which the moiety $$OCH_2CH(OH)-CH_2NR_1R_2$$

is attached on the Ar as defined above may be at the 4-, 5-, 6-, 7-, or 8-position, the preferred attachment is at the 4-position.

The present invention is also a pharmaceutical composition for the treatment of congestive heart failure, coronary heart disease, or myocardial ischemia which comprises an anticongestive heart failure, cardiotonic, or antiischemic effective amount of the compound of formula I as defined above together with a pharmaceutically acceptable carrier.

Additionally, the present invention is also a method of treating congestive heart failure, coronary heart disease, or myocardial ischemia in humans suffering therefrom which comprises administering the compound of formula I in unit dosage form.

DETAILED DESCRIPTION OF THE INVENTION

In the compounds of the formula I, the term "lower alkyl" is meant to include a straight or branched alkyl group having from one to four carbon atoms such as, for example, methyl, ethyl, propyl, or butyl, and isomers thereof.

"Halogen" includes chloro, fluoro, iodo, or bromo but preferably chloro or fluoro.

"Lower alkoxy" is 0-alkyl wherein alkyl is defined as above for lower alkyl.

"Aralkyl" is alkylenyl of from one to four carbons and an aryl group which is phenyl unsubstituted or substituted by lower alkoxy, halogen, trifluoromethyl, or lower alkyl.

"Cycloalkyl" is cyclopentyl, cyclohexyl, or cycloheptyl.

"Aryl" is independently as defined for Ar above.

The compounds of formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, methanesulfonic acid, malonic acid, fumaric acid, and the like, giving the hydrochloride, sulfamate, ethanesulfonate, benzenesulfonate, p-toluenesulfonate, methanesulfonate, malonate, fumarate, and the like, respectively (See for example, "Pharmaceutical Salts," *J. Pharm. Sci.* (1977) 66(1):1–19.)

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

In the compounds of the invention the carbon atoms in e.g. the 2-position of the propoxy side chain is asymmetrically substituted. The compounds may thus exist in the racemic form or in individual optical isomer form. The preferred optical isomer has the S-configuration at this asymmetrically substituted carbon atom of the propoxy side chain. Individual optical isomer forms may be obtained in conventional manner, for example, by using optically active starting materials or by fractional crystallization of diastereoisomeric salts formed with optically active acids.

The present invention is also the process for the preparation of a compound of the formula I as follows.

Generally, the compounds of formula I may be synthesized by alternate methods as shown in Schemes A, B, and C below.

Scheme A

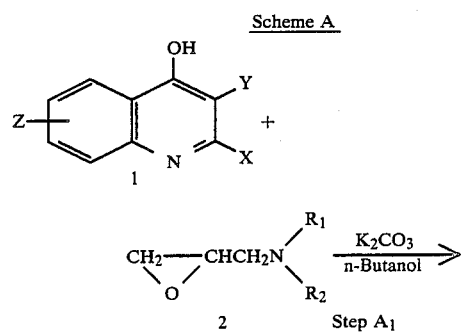

Step A₁

Scheme A -continued

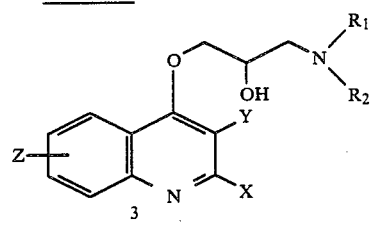

Scheme B

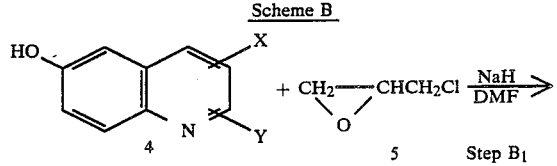

Step B₁

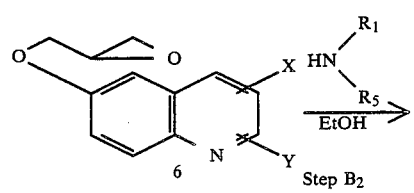

Step B₂

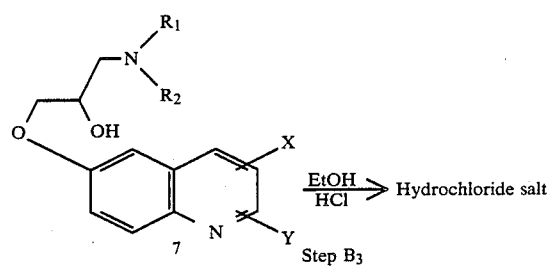

Step B₃

Scheme C

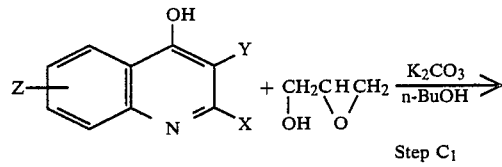

Step C₁

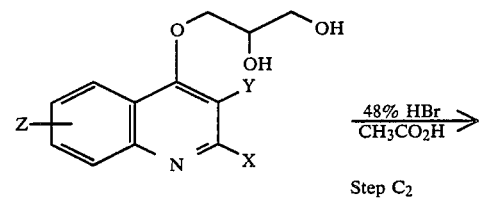

Step C₂

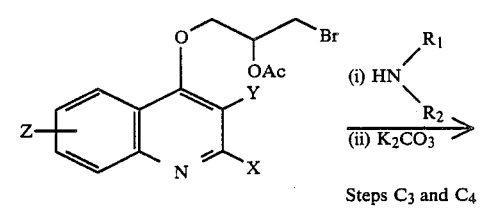

Steps C₃ and C₄

-continued
Scheme C

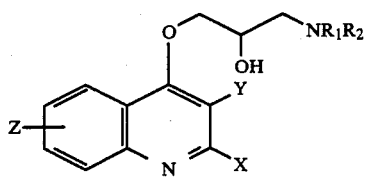

Each of Steps $A_1$, $B_1$, $B_2$, $B_3$, $C_1$, $C_2$, $C_3$, and $C_4$ use conditions within the skill of an ordinarily skilled artisan.

The starting materials in the above processes to prepare the compounds of the formula I are generally known, commercially available, or can be prepared by methods either known or analogous to those known.

Variations in the processes of the present invention are within the skill of an ordinary skilled artisan. The products of the processes are isolated by conventional means such as extraction, distillation, chromatography, and the like.

The following examples will further illustrate the invention, however, without limiting it thereto.

EXAMPLE 1

4-(Diphenylmethyl)-α-[4-quinolinyloxy)methyl]-1-piperazineethanol.

1.4 g (10 mmol) of 4-hydroxyquinoline, 3.4 g (11 mmol) of 1-diphenylmethyl-4-oxiranylmethylpiperazine as prepared in Preparation 1 shown below, and 1.4 g (10 mmol) of potassium carbonate in 20 ml n-butanol are heated under reflux for five hours. After cooling to room temperature the alcohol is distilled off under vacuum (12 mm) and the remaining residue is distributed between dichloromethane and water. The organic phase is separated, the solvent evaporated to dryness and the residue crystallized twice from ethanol. The product (2.0 g) forms colorless crystals, melting at 180°–181° C.

Calcd. for $C_{29}H_{31}N_3O_2$ (453.56):
C, 76.79; H, 6.89; N, 9.26.
Found C, 76.98; H, 6.85; N, 9.17.

PREPARATION 1

The epoxide (2) of Scheme A (wherein $R_1$ together with $R_2$ are

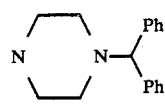

wherein Ph is phenyl).

12.6 g (50 mmol) of diphenylmethylpiperazine, 13.7 g (100 mmol) of epibromohydrin and 6.9 g (50 mmol) of potassium carbonate are refluxed in 250 ml of dry acetone for six hours.

After cooling, the inorganic material is filtered off, the filtrate is evaporated to dryness and the oily residue is crystallized twice from ethanol.

Yield: 11.0 g (35.6 mmol, 71.3%) colorless crystals, mp 110° C.

EXAMPLE 2

4-(Diphenylmethyl)-α-[(6-quinolinyloxy)methyl]-1-piperazineethanol trihydrochloride.

A solution of 2.9 g (20 mmol) of 6-hydroxyquinoline in N,N-dimethylformamide (40 ml) is added to a slurry of NaH (60% oil suspension, 0.88 g, 22 mmol) in 10 ml of DMF with stirring. After hydrogen evolution is ceased, epichlorohydrin is added and the reaction mixture is stirred at 60° C. for five hours. DMF is removed by distillation and the residue is treated with water. The organic matter is extracted with $CHCl_3$, chloroform layer is dried, and stripped to yield 3 g of the epoxy ether shown as compound (6) in Scheme B wherein X and Y are hydrogen. This is dissolved in 30 ml of ethanol and 4 g of benzhydryl piperazine and heated at reflux for sixteen hours. Ethanol is stripped and the residue chromatographed ($SiO_2$, $CH_2Cl_2/CH_3OH$; 9:1) to give the title compound in the free base form.

This was dissolved in EtOH (20 ml) and ethanolic HCl is added. The precipitate is filtered, washed with small volume of ethanol, and dried at 80° C. for four hours to give 0.8 g of the title compound; mp 202°–203° C. (dec).

Calcd. for $C_{29}H_{31}N_3O_2 \cdot 3HCl \cdot 0.5H_2O$: C, 60.94; H, 6.12; N, 7.34. Found C, 60.57; H, 6.13; N, 7.18.

Inotropic and vasodilatory activities are found for the compounds of formula I in both generally accepted in vitro and in vivo assays, thus these compounds are useful for the treatment of congestive heart failure, coronary heart disease, or myocardial ischemia. The protocol for the assays are as follows.

CARDIOVASCULAR ISOLATED HEART (CVIH)

The CVIH assay determines the effects of a compound of formula I on left ventricular contractility, heart rate, and coronary flow concurrently in an in vitro preparation.

PROTOCOL TO SCREEN COMPOUNDS FOR INOTROPIC, CHRONOTROPIC, AND VASCULAR ACTIVITIES IN THE ISOLATED LANGENDORFF RAT HEART PREPARATION (CARDIOVASCULAR ISOLATED HEART—CVIH)

Purpose

The purpose of the CVIH test is to determine effects of a compound on left ventricular contractility, heart rate, and coronary flow concurrently in an in vitro preparation.

Methods

Perfusion Technique

Male rats (400–600 gms) are pretreated with 2000 units Na heparin (Parke-Davis) and anesthetized with Na pentobarbital (50 mg/kg, Butler Co.) administered intraperitoneally. Once anesthetized, the rat heart is rapidly excised, the ascending aorta fitted to the aorta perfusion cannula, and secured with a ligature. The coronary arteries are perfused initially at a rate of about 15 ml/min for two to three minutes, after which they are perfused at constant pressure of 70 mm Hg and temperature of 37° C. The electrocardiogram (ECG) is recorded using two platinum electrodes positioned at the base and apex of the left ventricle (LV). The LV is instrumented via the mitral valve with a 4F Millar catheter tip pressure transducer. The catheter is advanced to the apex then withdrawn slightly Once properly positioned, the catheter is anchored to the perfusion cannulae with an alligater clip. A second heart is excised, cannulated, and perfused by the same method outlined above. Both hearts are tested in parallel The standard physiological salt solution (PSS) is a modified Krebs Henseleit bicarbonate buffer of the following composition in mM concentration: NaCl, 127; NaHCO$_3$, 25; dextrose, 5.5; Na Pyruvate, 2.0; KCl, 4.7; MgSO$_4$, 1.1; KH 2PO$_4$, 1.2; CaCl$_2$.2H$_2$O, 2.5; CaNa$_2$, EDTA, 0.05.

A thirty minute stabilization period is observed before starting the test protocol.

Microprocessor Controlled Coronary Perfusion and Drug Delivery System

The microprocessor control system is a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing concentrated drug solution (DC) at rates proportional to total coronary flow (CF$_T$). Drug concentrations, in this instance the compound of Example 1 and tetrodotidin, are increased by proportionate increases in the rate of DC infusion over CF$_T$ via the microprocessor keyboard. The proportional flow rates for DC:CF$_T$ is about 0.00005:1 at the low end and 0.0015:1 at the high end of the dose-response curve.

Dose response curves encompassing at least two log doses are carried out in one-half log increments starting at a subthreshold dose and ending at a dose which produces near maximal response.

Measurements

Measurements for CVIH are maximum positive first derivative of LVP (LV +dP/dt$_{max}$), heart rate (HR), and coronary flow (CF). Units are: LV +dP/dt$_{max}$, millimeters of mercury/second (mm Hg/sec); HR, beats/minute (bpm) and CF, milliliters/minute (ml/min). LV +dP/dt$_{max}$ is derived from the LVP signal by a differential amplifier and recorded HR is calculated from the ECG strip chart recording and CF is calculated by recording analog outputs from pumps 1 and 2. (Outputs from pump #1=CF$_T$ and the output from pump #2=CF for heart B (CF$_B$). CF for heart A (CF$_A$) is calculated (CF$_T$ CF$_B$=CF$_A$). All pumps are calibrated weekly or when pump tubing is replaced.

Compound Quantity and Preparation

The typical quantity necessary to screen a compound (N=2) is about 20 mg. Compounds are solubilized in DMSO and diluted with water when possible.

Data Reduction and Report Format

Data is digitized and averaged with an in-lab microcomputer (Buxco) data analyzer.

The results show percent change in HR, CF, and LV +dP/dt$_{max}$.

Using this procedure a representative compound of the formula I shown above as Example 1, exhibited a positive inotropic effect, increasing contractility by 5 to 81% over a concentration range of $1\times10^{-8}$ to $3\times10^{-7}$/M. The results are shown in the Table below.

TABLE CVIH

| Post-treatment Values are % Δ from Control | | | | | |
|---|---|---|---|---|---|
| Example-1 | | | | | |
| Concentration Molar | Control | 1. E-8 | 3. E-8 | 1. E-7 | 3. E-7 |
| HR    A | 269 | −4 | −2 | 0 | 13 |
|       B | 285 | 0 | 0 | −1 | −6 |
|       Mean |  | −2 | −1 | −1 | 4 |
| CF    A | 14.2 | −1 | −11 | −15 | 4 |
|       B | 12.8 | −1 | −0 | 0 | 9 |
|       Mean |  | −1 | −6 | −8 | 6 |
| LV    A | 1563 | 3 | 0 | 6 | 78 |
| +     B | 1560 | 7 | 4 | 46 | 83 |
| dP/dt Mean |  | 5 | 2 | 26 | 81 |
| Example-2 | | | | | |
| Concentration Molar | Control | 1. E-8 | 3. E-7 | 1. E-6 | 3. E-6 |
| HR    A | 269 | 0 | 0 | −3 | −5 |
|       B | 284 | 0 | 0 | −10 | −16 |
|       Mean | 277 | 0 | 0 | −7 | −11 |
| CF    A | 19.7 | 5 | 3 | 3 | 2 |
|       B | 13.5 | −5 | 2 | 4 | 2 |
|       Mean | 16.6 | 0 | 3 | 4 | 2 |
| LV    A | 1482 | 5 | 20 | 61 | 55 |
| +     B | 1686 | 1 | 5 | 52 | 63 |
| dP/dt Mean | 1584 | 3 | 13 | 57 | 59 |

TEST FOR IN VIVO MYOCARDIAL INOTROPIC ACTIVITY IN THE ANESTHETIZED DOG

This assay consists of determining the effects of increasing intravenous doses of compound on myocardial contractility (dP/dt$_{max}$ of left ventricular blood pressure), heart rate, and aortic blood pressure of the pentobarbital-anesthetized dog.

METHODS

Adult mongrel dogs of either sex are anesthetized with pentobarbital, 35 mg/kg, IV, and are subsequently maintained under anesthesia with a continuous infusion of pentobarbital, 3.5 mg/kg/hr. The trachea is intubated but the animals are permitted to breathe spontaneously. A cannula is inserted into the femoral vein for administering test agents. A Millar catheter tip pressure transducer or a fluid filled catheter is inserted into the ascending aorta via the femoral artery for measuring aortic blood pressure A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of the left ventricular blood pressure (dP/dt), obtained with a differentiator amplifier coupled to the corresponding pressure amplifier, are also recorded. A period of at least thirty minutes is utilized to obtain control data prior to administration of test compound.

The compounds are dissolved in dimethylacetamide. Each dose of the test compound is administered in a volume of 0.5 ml over a period of one minute Appropriate vehicle controls are administered when needed.

Again a representative compound of the formula I shown above as Example 1, at a dose of 1 mg/kg IV produced an increase in dP/dt of 128±25%, in heart rate of 0±0.7%, and a decrease in blood pressure of −6±0.7%.

Accordingly, the present invention further includes a novel method for treating congestive heart failure, coronary heart disease, or myocardial ischemia in mammals including humans suffering therefrom comprising the administration to such mammals either orally or parenterally a corresponding novel pharmaceutical composition having a compound of the formula I as defined above in appropriate unit dosage form.

The appropriate unit dosage form is one from among those known such as, for example, as described in copending PD-3316.

The quantity of active compound in a unit dose of preparation may be varied or adjusted from 30 mg to 100 mg according to the particular application and the potency of the active ingredient. The compositions can, if desired, also contain other compatible therapeutic agents.

In therapeutic use as described above, the mammalian dosage range for a 70 kg subject is ordinarily from 0.03 to 30 mg/kg of body weight per day or preferably 0.3 to 15 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

We claim:

1. A compound of the formula

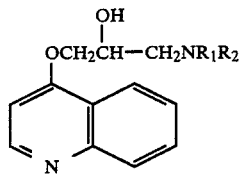

and pharmaceutically acceptable salts thereof;
wherein $R_1$ and $R_2$ are independently
 (i) lower alkyl; aralkyl wherein alkyl is alkylenyl of from one to four carbons and ar is phenyl unsubstituted or substituted by lower alkoxy, halogen, trifluoromethyl or lower alkyl; cyclopentyl, cyclohexyl or cycloheptyl;
 (ii) taken together to form a ring which is

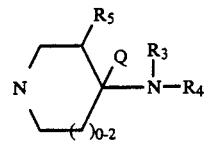

wherein $R_3$ and $R_4$ are independently hydrogen, lower alkyl, aralkyl, cycloalkyl and wherein $R_5$ and Q are independently hydrogen, lower alkyl or together form an additional bond;
 (iii) taken together to form

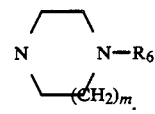

wherein m is 1 or 2 and $R_6$ is
 (a) lower alkyl substituted by one or two aryl wherein aryl is phenyl optionally substituted by lower alkyl, halogen, trifluoromethyl of lower alkoxy,
 (b) phenyl optionally substituted by lower alkyl, halogen, trifluoromethyl, lower alkoxy; or
 (c) $C(O)R_7$ wherein $R_7$ is lower alkyl, lower alkoxy, or monoloweralkylamino, or diloweralkylamino.

2. A compound of claim wherein the $NR_1R_2$ is

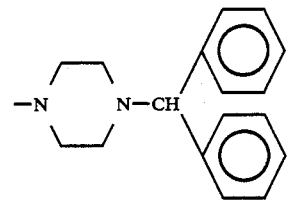

3. A trihydrochloride of the compound of claim 1.

4. A compound of claim 1 which is 4-(diphenylmethyl-α-[(4-quinolinyloxy)methyl]-1-piperazineethanol.

5. A pharmaceutical composition for treating congestive heart failure, coronary heart disease, or myocardial ischemia which comprises an amount effective to treat congestive heart failure, coronary heart disease, or myocardial ischemia of a compound of claim 1 and a pharmaceutically acceptable carrier.

6. A method of treating congestive heart failure, coronary heart disease, or myocardial ischemia in a mammal suffering therefrom comprising the administration of a compound of claim 1 in unit dosage form.

* * * * *

UNITED STATES PATENT AND TRADEMARK OFFICE
CERTIFICATE OF CORRECTION

PATENT NO. : 4,980,351

DATED : December 25, 1990

INVENTOR(S) : Hubert G. K. Barth, et al

It is certified that error appears in the above-identified patent and that said Letters Patent is hereby corrected as shown below:

In column 10, line 30, after "claim" add --1--.

In column 10, line 44, after "yl" add --)--.

Signed and Sealed this

Fourteenth Day of July, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,980,351

DATED : December 25, 1990

INVENTOR(S) : Hubert G. K. Barth, et al

It is certified that error appears in the above-identified patent and that said Letters Patent is hereby corrected as shown below:

In column 10, line 23, change "of" to --or--.

Signed and Sealed this

Twenty-fifth Day of August, 1992

*Attest:*

DOUGLAS B. COMER

*Attesting Officer*     *Acting Commissioner of Patents and Trademarks*